(12) United States Patent
Mizoguchi

(10) Patent No.: US 10,807,043 B2
(45) Date of Patent: Oct. 20, 2020

(54) HOLLOW-FIBER-TYPE BLOOD PROCESSING DEVICE AND METHOD

(71) Applicant: TERUMO KABUSHIKI KAISHA, Tokyo (JP)

(72) Inventor: Kazuhiro Mizoguchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/684,018

(22) Filed: Aug. 23, 2017

(65) Prior Publication Data

US 2017/0348639 A1 Dec. 7, 2017

Related U.S. Application Data

(63) Continuation of application No. PCT/JP2016/055183, filed on Feb. 23, 2016.

(30) Foreign Application Priority Data

Feb. 24, 2015 (JP) .................................. 2015-033811

(51) Int. Cl.
*B01D 63/02* (2006.01)
*A61M 1/16* (2006.01)
(Continued)

(52) U.S. Cl.
CPC ......... *B01D 63/021* (2013.01); *A61M 1/1623* (2014.02); *A61M 1/3627* (2013.01);
(Continued)

(58) Field of Classification Search
CPC ...... B01D 63/021; B01D 65/00; B01D 61/30; A61M 1/3627; A61M 1/1623
See application file for complete search history.

(56) References Cited

U.S. PATENT DOCUMENTS 4,415,954 A * 11/1983 Schaefer .................. F21L 2/00
362/189
6,918,886 B1 * 7/2005 Baurmeister ......... A61M 1/342
210/321.72
(Continued)

FOREIGN PATENT DOCUMENTS

EP   1852949 A1      11/2007
EP   2692371 B1 *   11/2015   .......... A61M 1/1698
(Continued)

OTHER PUBLICATIONS

Written Opinion of the International Searching Authority, PCT/JP2016/055183, dated Feb. 23, 2016, pp. 1-7.
(Continued)

*Primary Examiner* — Chester T Barry
(74) *Attorney, Agent, or Firm* — MacMillan, Sobanski & Todd, LLC

(57) ABSTRACT

A hollow-fiber-type blood processing device and methods for its manufacture include a hollow fiber membrane bundle which is obtained by bundling a large number of hollow fiber membranes into a columnar shape. A sheet body is mounted on an outer peripheral portion of the hollow fiber membrane bundle. The sheet body is expandable as a result of being woven from a sheet material. An inner diameter of the sheet body in a natural state where no external force is applied to the sheet body is smaller than the outer diameter of the hollow fiber membrane bundle.

11 Claims, 14 Drawing Sheets

(51) Int. Cl.
*A61M 1/36* (2006.01)
*B01D 61/30* (2006.01)
*B01D 65/00* (2006.01)
*B29C 70/68* (2006.01)

(52) U.S. Cl.
CPC .............. *B01D 61/30* (2013.01); *B01D 65/00* (2013.01); *A61M 1/1621* (2014.02); *A61M 1/1698* (2013.01); *B01D 2313/23* (2013.01); *B29C 70/681* (2013.01)

(56) References Cited

U.S. PATENT DOCUMENTS

| | | | | |
|---|---|---|---|---|
| 8,425,838 | B2* | 4/2013 | Mizoguchi | A61M 1/1698 422/44 |
| 2003/0196949 | A1 | 10/2003 | Sunohara et al. | |
| 2004/0149645 | A1 | 8/2004 | Sunohara et al. | |
| 2006/0016743 | A1 | 1/2006 | Ogihara et al. | |
| 2007/0231203 | A1 | 10/2007 | Mizoguchi et al. | |
| 2008/0237902 | A1* | 10/2008 | Nagumo | B01D 53/22 261/104 |
| 2014/0091024 | A1 | 4/2014 | Mizoguchi et al. | |
| 2015/0010433 | A1 | 1/2015 | Takeuchi et al. | |
| 2015/8001043 | | 1/2015 | Takeuchi et al. | |
| 2015/0068670 | A1 | 3/2015 | Mizoguchi et al. | |
| 2017/0239077 | A1* | 8/2017 | Tang | A61F 6/04 |
| 2018/0028215 | A1* | 2/2018 | Cohen | A61B 17/32001 |

FOREIGN PATENT DOCUMENTS

| | | |
|---|---|---|
| JP | 8168525 A | 2/1996 |
| WO | 9822161 A1 | 5/1998 |
| WO | 2012132110 A1 | 4/2012 |

OTHER PUBLICATIONS

European Patent Office Search Report, PCT/JP2016055183, dated Sep. 18, 2018.
The State Intellectual Property Office of People's Republic of China, 201680012299.X, The First Office Action.
Translation of Office Action of Japanese Patent Office, JP application 2017-502371.

* cited by examiner

HOLLOW-FIBER-TYPE BLOOD PROCESSING DEVICE AND METHOD

This application is a continuation of PCT Application No. PCT/JP2016/055183, filed Feb. 23, 2016, based on and claiming priority to Japanese application no. 2015-033811, filed Feb. 24, 2015, both of which are incorporated herein by reference in their entirety.

TECHNICAL FIELD

The present invention relates to a method for manufacturing a hollow-fiber-type blood processing device and the hollow-fiber-type blood processing device.

BACKGROUND ART

In the related art, an artificial lung having a configuration of performing gas exchange using a hollow fiber membrane layer in which a large number of hollow fiber membranes are stacked is known.

This artificial lung includes a housing, a hollow fiber membrane bundle which has a cylindrical shape and is housed in the housing, a blood inlet port, a blood outlet port, a gas inlet port, and a gas outlet port. Gas exchange, that is, addition of oxygen and decarbonation, is performed between blood and gas through each hollow fiber membrane.

However, in the artificial lung having such a configuration, in some cases, air bubbles are entrained in blood flowing in from the blood inlet port. In this case, the air bubbles are preferably removed by the device. The hollow fiber membrane bundle itself is designed so as to efficiently perform gas exchange and is not originally intended to remove air bubbles. Therefore, in the hollow fiber membrane bundle, air bubbles are not sufficiently removed, and thus, there is a problem in that air bubbles entrained in the blood might flow out from the blood inlet port, and can then be transferred downstream to a patient. A band-like filter member capable of capturing air bubbles in blood has been wound around the outer peripheral portion of the hollow fiber membrane bundle (see, for example, publication WO2012/132110A1). In order to discharge the captured air bubbles through the hollow fiber membranes, such a filter member is preferably brought into close contact with the hollow fiber membrane bundle.

However, in some cases, a gap is formed between the filter member and the hollow fiber membrane bundle, such as in a case of simply winding the band-like filter member around the hollow fiber membrane bundle for fixation.

SUMMARY OF INVENTION

Technical Problem

An object of the present invention is to provide a method for manufacturing a hollow-fiber-type blood processing device in which a hollow fiber membrane bundle can be reliably brought into close contact with a sheet body, and a hollow-fiber-type blood processing device in which a hollow fiber membrane bundle is reliably brought into close contact with a sheet body.

Solution to Problem

According to one aspect of the invention, a method for manufacturing a hollow-fiber-type blood processing device comprises the steps of mounting a sheet body on the outer peripheral portion of a hollow fiber membrane bundle, wherein the sheet material is mounted in a state where the sheet material is previously formed as a cylindrical member.

According to the method, the sheet material is expandable, and in its natural shape the inner diameter of the sheet material is cylindrical, and in a natural state wherein no external force is applied to the sheet material it has a diameter smaller than the outer diameter of the hollow fiber membrane bundle.

The mounting of the sheet material is performed while fastening the hollow fiber membrane bundle in a direction from the outer peripheral portion side of the hollow fiber membrane bundle toward a central axis side using the sheet material.

In the mounting step, the sheet material preferably enters an inverted state where the front and the back of the sheet material are inverted, prior to the mounting of the sheet material, and the mounting of the sheet material is performed while returning the inverted state to an original state where the front and the back are not inverted.

In the mounting step, a release sheet may preferably be mounted on the outer peripheral portion of the hollow fiber membrane bundle over its whole circumference, prior to the mounting of the sheet material, and the sheet material is mounted on the release sheet in an overlapping manner, and thereafter, the release sheet is removed while leaving the sheet material.

The method may preferably include friction reduction processing for reducing friction is performed on both surfaces of the release sheet.

According to another aspect of the invention, a hollow-fiber-type blood processing device includes a hollow fiber membrane bundle which is obtained by bundling a large number of hollow fiber membranes to have an outer shape formed in a cylindrical shape or a columnar shape; and a sheet body mounted on an outer peripheral portion of the hollow fiber membrane bundle, in which the mounting of the sheet material is performed in a state where the hollow fiber membrane bundle is fastened in a direction from the outer peripheral portion side of the hollow fiber membrane bundle toward a central axis side.

The hollow fiber membrane bundle preferably includes an inner hollow fiber membrane bundle and an outer hollow fiber membrane bundle which are concentrically disposed with each other. The sheet body preferably includes an inner sheet body mounted on the outer peripheral portion of the inner hollow fiber membrane bundle and an outer sheet body mounted on the outer peripheral portion of the outer hollow fiber membrane bundle, and a fastening degree of the inner sheet body with respect to the inner hollow fiber membrane bundle is smaller than that of the outer sheet body with respect to the outer hollow fiber membrane bundle.

Each of the inner sheet body and the outer sheet body preferably forms a mesh shape, and an opening of the inner sheet body is larger than that of the outer sheet body.

The hollow fiber membrane bundle is preferably configured to allow blood to pass between the hollow fiber membranes and has a heat exchange function of exchanging heat with the blood. The hollow-fiber-type blood processing device may typically be used as an artificial lung.

Advantageous Effects of Invention

According to the present invention, the sheet body can fasten the hollow fiber membrane bundle in a direction from the outer peripheral portion side of the hollow fiber membrane bundle toward the central axis side, and this fastening state is reliably maintained thereafter. Accordingly, the sheet body can be reliably brought into close contact with the hollow fiber membrane bundle, and therefore, various functions of the sheet body can be reliably exhibited.

DESCRIPTION OF EMBODIMENTS

Hereinafter, a method for manufacturing a hollow-fiber-type blood processing device of the present invention and a hollow-fiber-type blood processing device of the present invention will be described in detail based on preferred embodiments shown in accompanying drawings.

First Embodiment

Figure 1:
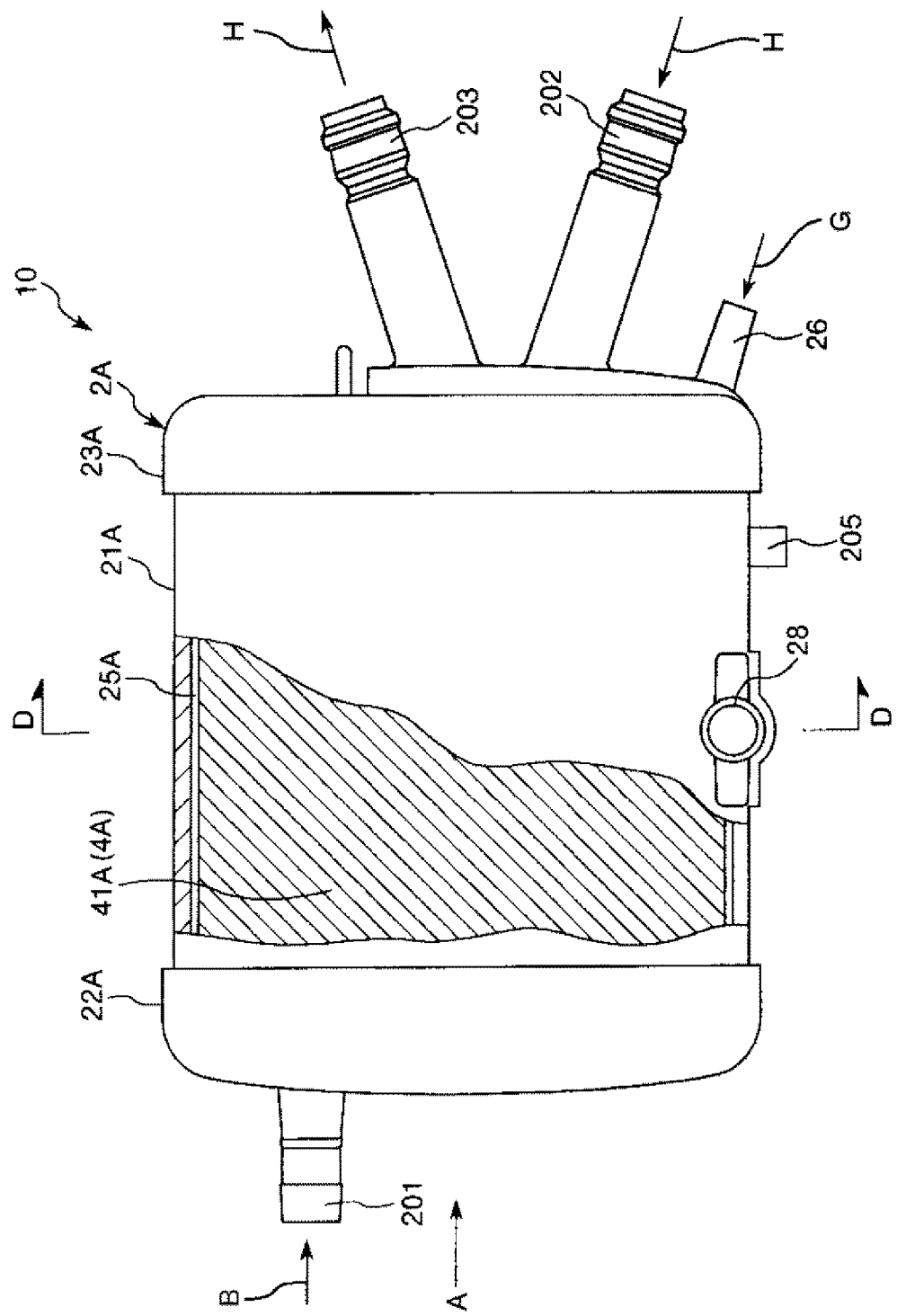
FIG. 1 is a plan view showing an embodiment in a case where a hollow-fiber-type blood processing device of the present invention is applied to an artificial lung.
Figure 2:
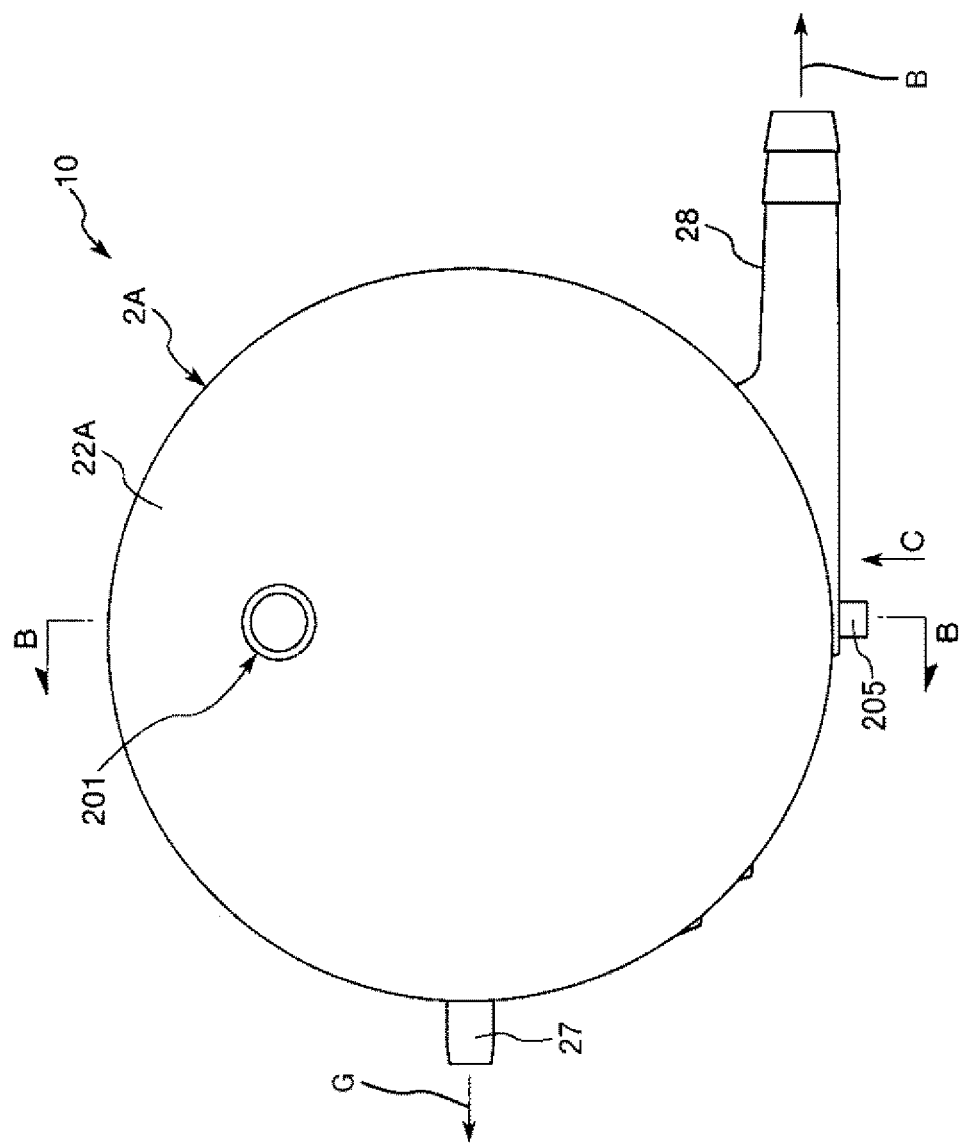
FIG. 2 is a view of the artificial lung shown in FIG. 1 when seen from a direction of arrow A.
Figure 3:
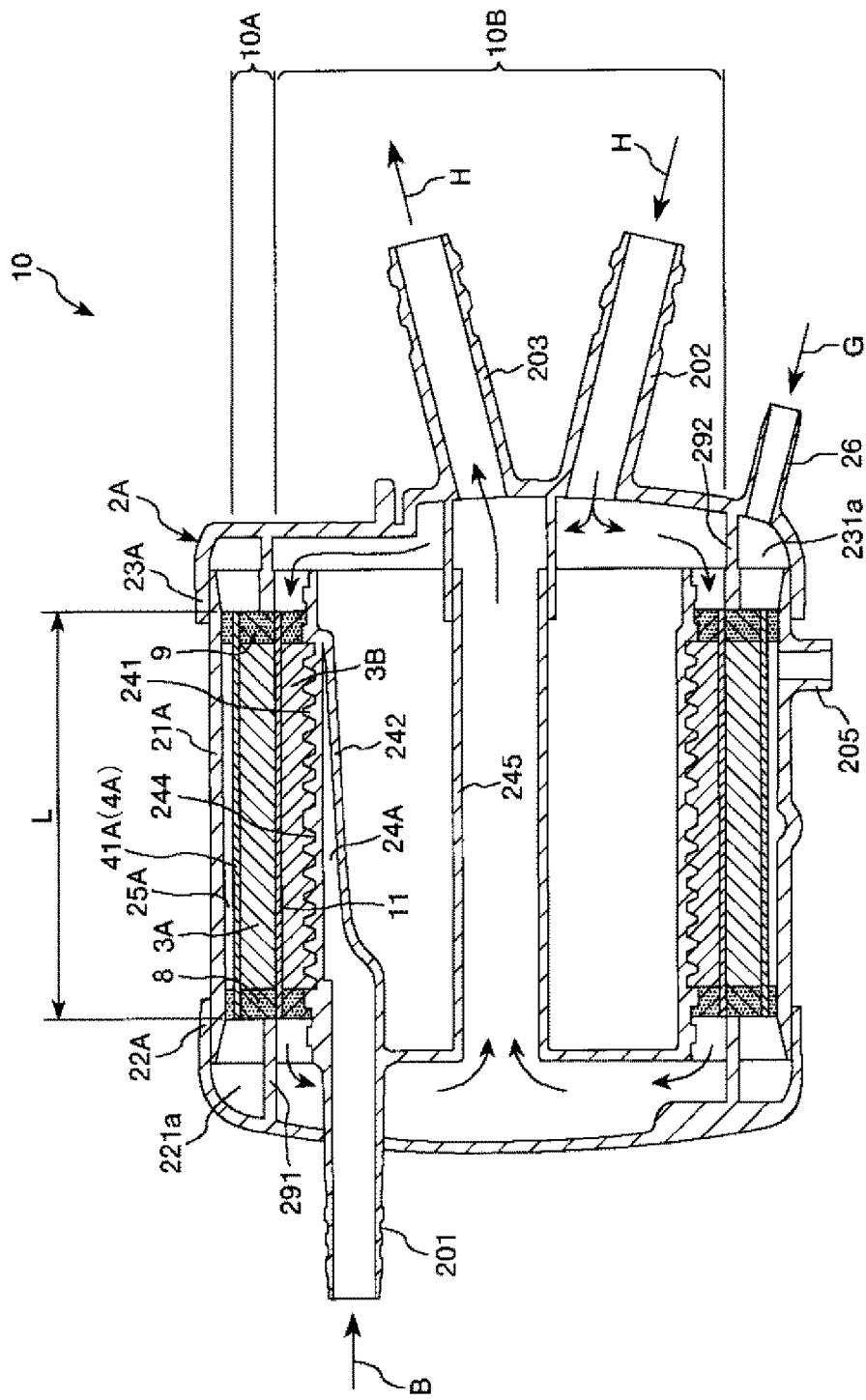
FIG. 3 is a cross-sectional view taken along line B-B in FIG. 2.
Figure 4:
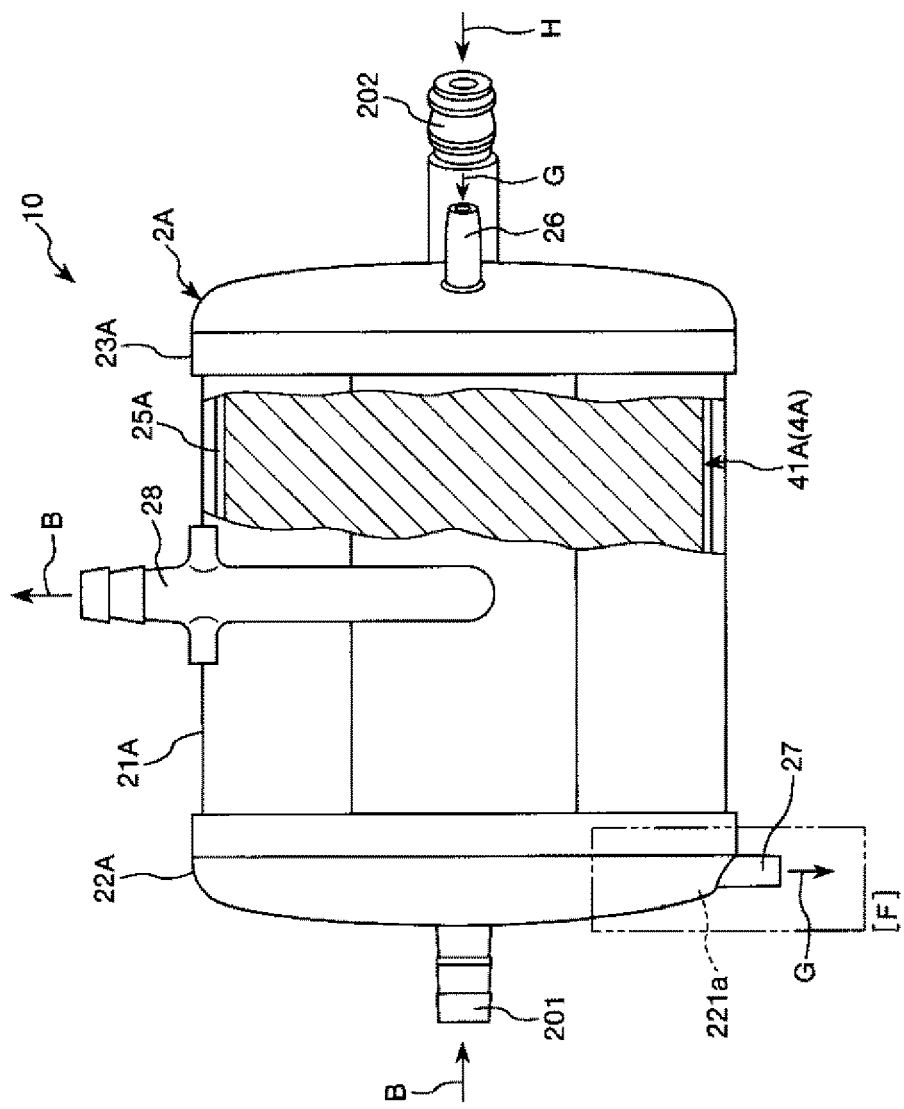
FIG. 4 is a view when seen from a direction of arrow C in FIG. 2.
Figure 5:
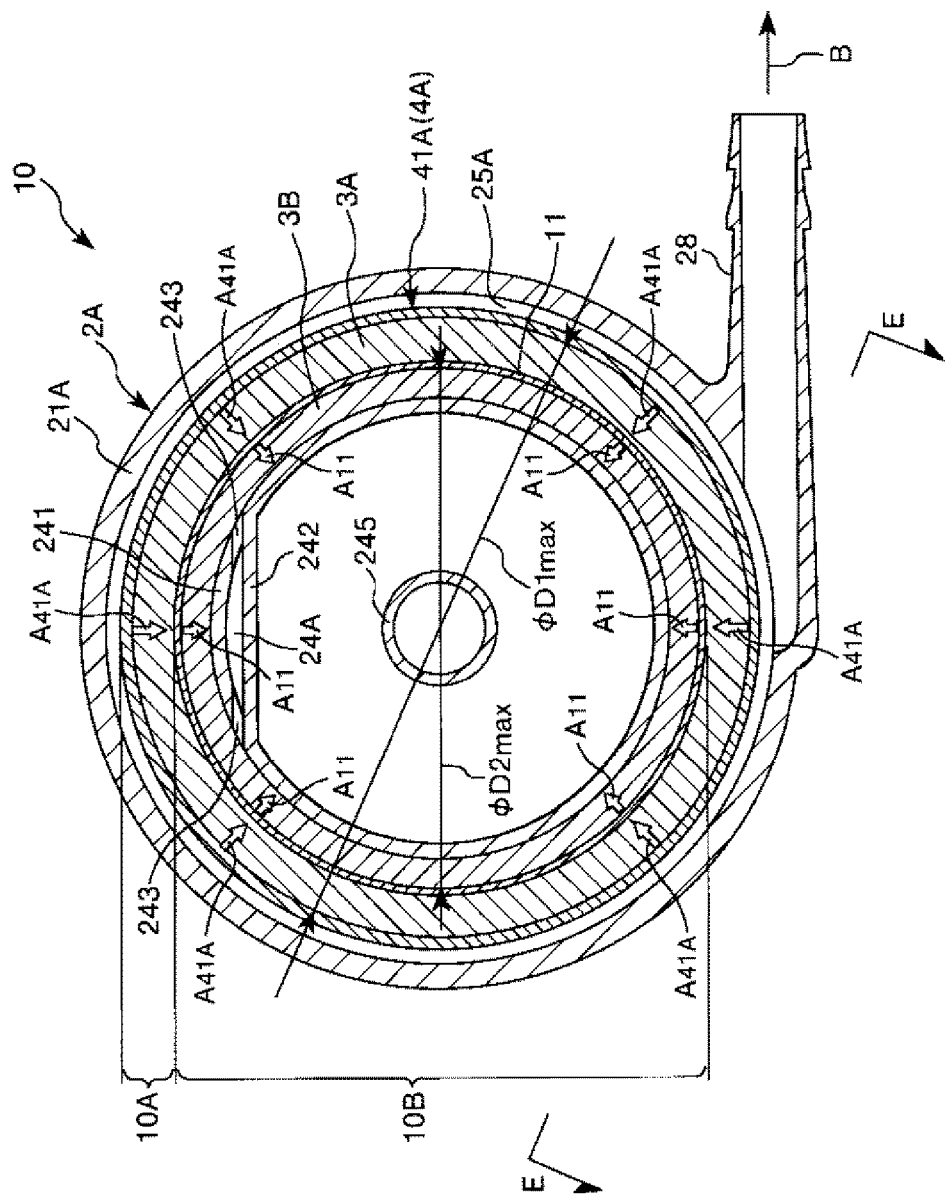
FIG. 5 is a cross-sectional view taken along line D-D in FIG. 1.
Figure 6:
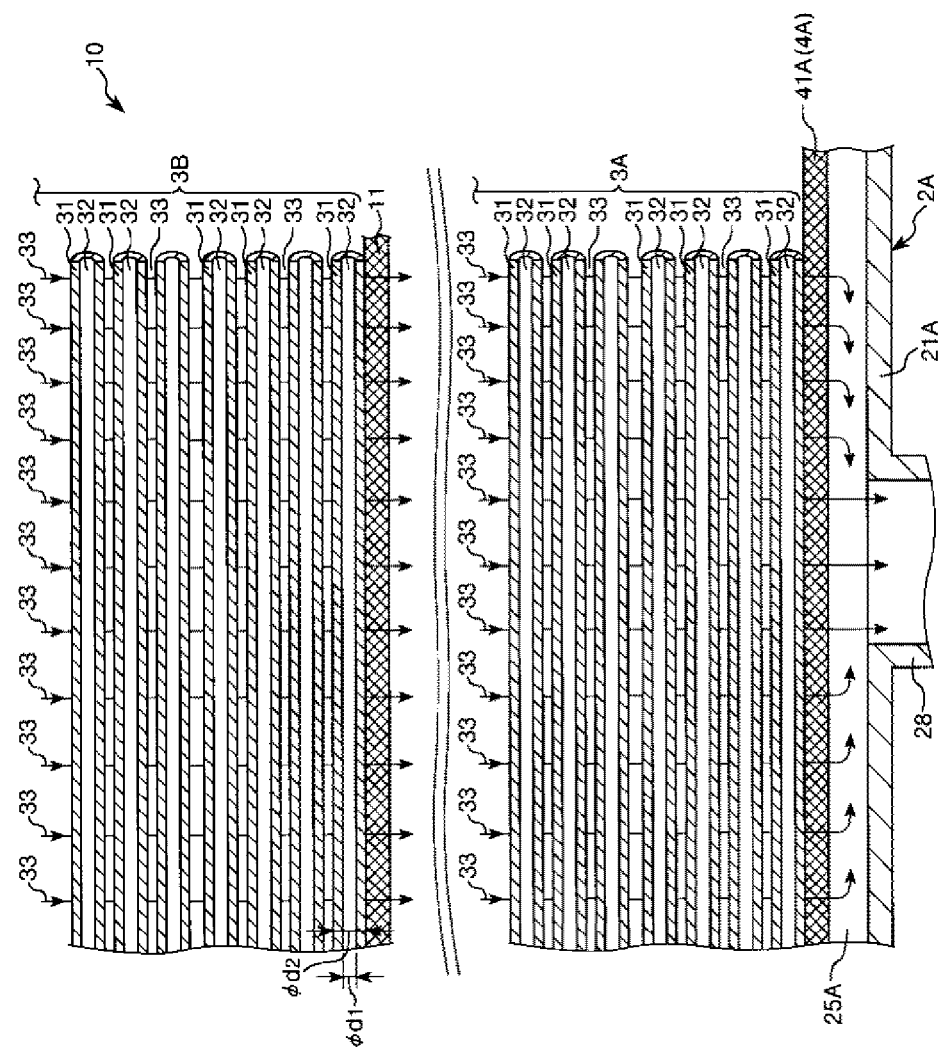
FIG. 6 is a cross-sectional view taken along line E-E in FIG. 5.

FIG. 1 is a plane view showing an embodiment in a case where a hollow-fiber-type blood processing device of the present invention is applied to an artificial lung. FIG. 2 is a view of the artificial lung shown in FIG. 1 when seen from a direction of arrow A. FIG. 3 is a cross-sectional view taken along line B-B in FIG. 2. FIG. 4 is a view when seen from a direction of arrow C in FIG. 2. FIG. 5 is a cross-sectional view taken along line D-D in FIG. 1. FIG. 6 is a cross-sectional view taken along line E-E in FIG. 5. FIGS. 7 to 14 are longitudinal cross-sectional views showing a process (including the method for manufacturing a hollow-fiber-type blood processing device of the present invention) of manufacturing the artificial lung shown in FIG. 1 in order. Note that, in FIGS. 1, 3, 4, and 14, the left side is referred to as "left" or a "left portion (one side)" and the right side is referred to as "right" or a "right portion (the other side)". In addition, in FIGS. 7 to 13 (the same also applies to FIGS. 15 to 18), the upper side is referred to as "upper" or an "upper portion" and the lower side is referred to as "lower" or a "lower portion". In addition, in FIGS. 1 to 6, the inside of the artificial lung will be described as a "blood inflow side" or an "upstream side" and the outside will be described as a "blood outflow side" or a "downstream side".

The entire shape of an artificial lung 10 shown in FIGS. 1 to 5 is in a substantially columnar (i.e., cylindrical) shape. This artificial lung 10 is a heat exchanger-attached artificial lung including: a heat exchange portion 10B which is provided inside the artificial lung and performs heat exchange on blood; and an artificial lung portion 10A which is provided on an outer peripheral side of the heat exchange portion 10B and is used as a gas exchange portion performing gas exchange on blood. The artificial lung 10 is installed, for example, in an extracorporeal blood circulation circuit.

The artificial lung 10 has a housing 2A in which the artificial lung portion 10A and the heat exchange portion 10B are housed.

The housing 2A includes: a cylindrical housing main body 21A; a dish-like first lid body 22A which seals a left end opening of the cylindrical housing main body 21A; and a dish-like second lid body 23A which seals a right end opening of the cylindrical housing main body 21A.

The cylindrical housing main body 21A, the first lid body 22A, and the second lid body 23A are formed of a resin material. The first lid body 22A and the second lid body 23A are fixed to the cylindrical housing main body 21A through a method such as welding or adhesion using an adhesive.

A tubular blood outlet port 28 is formed on the outer peripheral portion of the cylindrical housing main body 21A. This blood outlet port 28 protrudes toward a substantially tangential direction of the outer peripheral surface of the cylindrical housing main body 21A (refer to FIG. 5).

A tubular purge port 205 is protrusively formed on the outer peripheral portion of the cylindrical housing main body 21A. The purge port 205 is formed on the outer peripheral portion of the cylindrical housing main body 21A such that a central axis of the purge port 205 intersects with a central axis of the cylindrical housing main body 21A.

A tubular gas outlet port 27 is protrusively formed on the first lid body 22A. The gas outlet port 27 is formed on the outer peripheral portion of the first lid body 22A such that a central axis of the first lid body 22A intersects with the center of the first lid body 22A (refer to FIG. 2).

In addition, a blood inlet port 201 protrudes from an end surface of the first lid body 22A such that a central axis of the blood inlet port is eccentric to the center of the first lid body 22A.

A tubular gas inlet port 26, a heat medium inlet port 202, and a heat medium outlet port 203 are protrusively formed on the second lid body 23A. The gas inlet port 26 is formed at an edge portion of the end surface of the second lid body 23A. The heat medium inlet port 202 and the heat medium outlet port 203 are formed at a substantially central portion of the end surface of the second lid body 23A. In addition, central lines of the heat medium inlet port 202 and the heat medium outlet port 203 are slightly inclined to a central line of the second lid body 23A.

Note that, in the present invention, the entire shape of the housing 2A does not necessarily have a complete columnar shape, and may have, for example, a partially missing shape or a shape to which an irregular portion is added.

As shown in FIGS. 3 and 5, the artificial lung portion 10A having a cylindrical shape along the inner peripheral surface of the housing 2A is housed inside the housing 2A. The artificial lung portion 10A includes: a cylindrical hollow fiber membrane bundle (outer hollow fiber membrane bundle) 3A; and a filter member (outer sheet body) 41A used as air bubble removing means 4A provided on the outer peripheral side of the hollow fiber membrane bundle 3A. The hollow fiber membrane bundle 3A and the filter member 41A are disposed in order of the hollow fiber membrane bundle 3A and the filter member 41A from a blood inflow side.

In addition, the cylindrical heat exchange portion 10B disposed along the inner peripheral surface of the artificial lung portion 10A, that is, concentrically disposed with the artificial lung portion is installed inside the artificial lung portion. The heat exchange portion 10B has: a cylindrical hollow fiber membrane bundle (inner hollow fiber membrane bundle) 3B; and an intermediate sheet member (inner sheet body) 11 which is provided on the outer peripheral side of the hollow fiber membrane bundle 3B. The hollow fiber membrane bundle 3B and the intermediate sheet member 11 are disposed in order of the hollow fiber membrane bundle 3B and the hollow fiber membrane bundle 3B from the blood inflow side.

As shown in FIG. 6, each of the hollow fiber membrane bundles 3A and 3B is constituted of a large number of hollow fiber membranes 31 and is formed by bundling these hollow fiber membranes 31, that is, accumulating and stacking these hollow fiber membranes 31 in a layered shape. The number of layers stacked is not particularly limited, but is preferably, for example, 3 to 40 layers. Note that each of the hollow fiber membranes 31 of the outer hollow fiber membrane bundle 3A has a gas exchange function of performing gas exchange. On the other hand, each of the hollow fiber membranes 31 of the inner hollow fiber membrane bundle 3B has a heat exchange function of performing heat exchange.

As shown in FIG. 3, both end portions of the hollow fiber membrane bundles 3A and 3B are collectively fixed to the inner surface of the cylindrical housing main body 21A using partition walls 8 and 9. The partition walls 8 and 9 are formed of, for example, of potting materials such as polyurethane and silicone rubber, or adhesives. Furthermore, the inner peripheral portion of the inner hollow fiber membrane bundle 3B is engaged with an irregular portion 244 formed on the outer peripheral portion of a first cylindrical member 241. The hollow fiber membrane bundle 3B is reliably fixed to the cylindrical housing main body 21A through fixation using the partition walls 8 and 9 and this engagement. Accordingly, it is possible to reliably prevent positional deviation of the hollow fiber membrane bundle 3B caused while using the artificial lung 10. In addition, the irregular portion 244 also functions as a flow path for circulating a blood B throughout the hollow fiber membrane bundle 3B.

Note that, as shown in FIG. 5, the maximum outer diameter φD1max of the outer hollow fiber membrane bundle 3A is preferably 20 mm to 200 mm, and more preferably 40 mm to 150 mm. The maximum outer diameter φD2max of the inner hollow fiber membrane bundle 3B is preferably 10 mm to 150 mm, and more preferably 20 mm to 100 mm. In addition, as shown in FIG. 3, a length L of the hollow fiber membrane bundles 3A and 3A along a central axis direction is preferably 30 mm to 250 mm, and more preferably 50 mm to 200 mm. With such conditions, the hollow fiber membrane bundle 3A has an excellent gas exchange function and the hollow fiber membrane bundle 3B has an excellent heat exchange function.

A blood flow path 33 through which the blood B flows from the upper side to the lower side in FIG. 6 is formed on the outside of each of the hollow fiber membranes 31 between the partition wall 8 and the partition wall 9 in the housing 2A, that is, in a gap between the hollow fiber membranes 31.

A blood inflow side space 24A communicating with the blood inlet port 201 is formed on the upstream side of the blood flow path 33 as a blood inlet portion of the blood B flowing in from the blood inlet port 201 (refer to FIGS. 3 and 5).

The blood inflow side space 24A is a space defined by the first cylindrical member 241 forming a cylindrical shape and a plate piece 242 which is disposed inside the first cylindrical member 241 and is disposed so as to face a part of the inner peripheral portion of the first cylindrical member. The blood B flowing in the blood inflow side space 24A can flow down throughout blood flow paths 33 through a plurality of side holes 243 formed in the first cylindrical member 241.

In addition, a second cylindrical member 245 concentrically disposed with the first cylindrical member 241 is disposed inside the first cylindrical member 241. As shown in FIG. 3, a heat medium H, for example, water, flowing in from the heat medium inlet port 202 is discharged from the heat medium outlet port 203 after passing through a flow path (hollow portion) 32 each of the hollow fiber membranes 31 of the hollow fiber membrane bundle 3B on the outer peripheral side of the first cylindrical member 241, and the inside of the second cylindrical member 245 in order. In addition, heat exchange (heating or cooling) is performed between the blood B coming into contact with the hollow fiber membranes 31 in the blood flow paths 33 and the heat medium H when the heat medium H passes through the flow path 32 of each of the hollow fiber membranes 31.

The filter member 41A having a function of capturing air bubbles existing in the blood B flowing through the blood flow paths 33 is disposed on the downstream side of the blood flow paths 33.

The filter member 41A is formed of a sheet body and is mounted so as to cover the entirety of the outer peripheral portion of the hollow fiber membrane bundle 3A. Both end portions of the filter member 41A are also fixed to the partition walls 8 and 9, and thus, are fixed to the housing 2A (refer to FIG. 3).

In addition, the inside surface of the filter member 41A is brought into close contact with the outer peripheral portion of the outer hollow fiber membrane bundle 3A (refer to FIGS. 3, 5, and 6). Accordingly, even if there are air bubbles in blood flowing through the blood flow paths 33, the air bubbles can be reliably captured by the filter member 41A (refer to FIG. 6). The air bubbles captured by the filter member 41A are pushed into each of the hollow fiber membranes 31 in the vicinity of the filter member 41A by blood. As a result, the air bubbles are removed from the blood flow paths 33.

In addition, a cylindrical gap is formed between the outer peripheral portion of the filter member 41A and the inner peripheral portion of the cylindrical housing main body 21A and forms a blood outflow side space 25A. A blood outlet portion is formed by this blood outflow side space 25A and the blood outlet port 28 communicating with the blood outflow side space 25A. When the blood outlet portion has the blood outflow side space 25A, a space through which the blood B that has been transmitted through the filter member 41A flows toward the blood outlet port 28 is secured, and therefore, it is possible to smoothly discharge the blood B.

The intermediate sheet member 11 is disposed between the outer hollow fiber membrane bundle 3A and the inner hollow fiber membrane bundle 3B. The intermediate sheet member 11 is formed of a sheet body and is mounted so as to cover the entirety of the outer peripheral portion of the inner hollow fiber membrane bundle 3B. Both end portions of the intermediate sheet member 11 are also fixed to the partition walls 8 and 9 similarly to the filter member 41A, and thus, are fixed to the housing 2A (refer to FIG. 3).

In addition, the inside surface of the intermediate sheet member 11 is brought into close contact with the outer peripheral portion of the inner hollow fiber membrane bundle 3B (refer to FIGS. 3, 5, and 6). The intermediate sheet member 11 mainly used for maintaining the shape of the hollow fiber membrane bundle 3B during a process of manufacturing the artificial lung 10 as will be described below. For this reason, when the intermediate sheet member 11 is brought into close contact with the hollow fiber membrane bundle 3B, the shape of the hollow fiber membrane bundle 3B can be reliably maintained.

In the artificial lung 10, each of the filter member 41A and the intermediate sheet member 11 is formed in a mesh shape by crossing warp and weft. Examples thereof include a woven fabric in which warp and weft are plain-woven and a product (including screen mesh) in which warp and weft are crossed in a lattice shape.

The openings within the mesh (i.e., the spacings between adjacent threads of a woven fabric) of the intermediate sheet member 11 is larger than those of the filter member 41A. The intermediate sheet member 11 is used for maintaining the shape of the hollow fiber membrane bundle 3B as described above. Therefore, it is preferable to set the openings within the mesh to be large so as not to disturb the flow of the blood B flowing down from the hollow fiber membrane bundle 3B to the hollow fiber membrane bundle 3A as much as possible.

On the other hand, the filter member 41A is formed such that it is possible to more reliably capture air bubbles and to make the blood B more easily pass through the filter member than the air bubbles by making the openings within the mesh of the filter member be small.

In addition, the thickness of the filter member 41A and the intermediate sheet member 11 is, for example, preferably 0.03 to 0.8 mm and more preferably 0.05 to 0.5 mm. Accordingly, mounting of each member can be easily performed during the process of manufacturing the artificial lung 10 and the function of each member after the artificial lung 10 has been manufactured is reliably exhibited.

Examples of the constituent materials (constituent materials of warp and weft) of the filter member 41A and the intermediate sheet member 11 include: polyolefins such as polyamide, polyethylene, and polypropylene; polyester such as polyethylene terephthalate and polybutylene terephthalate; polyamide; cellulose; polyurethane; and aramid fibers. One or more thereof can be used singly or in combination (for example, making the compositions of warp and weft be different from each other). Particularly, it is preferable to use (contain) any one of polyethylene terephthalate, polyethylene, polypropylene, polyamide, and polyurethane as the constituent materials in that these materials have excellent antithrombotic properties and it is difficult to generate clogging.

In addition, the filter member 41A and the intermediate sheet member 11 preferably have hydrophilicity. That is, it is preferable that the filter member 41A and the intermediate sheet member 11 themselves are formed of a material having hydrophilicity or are subjected to hydrophilic treatment (for example, plasma treatment or the like). Accordingly, the passing resistance of the blood B in each member is reduced.

As shown in FIG. 3, an annular rib 291 is protrusively formed inside the first lid body 22A. A first chamber 221a which is airtightly sealed is defined by the first lid body 22A, the rib 291, and the partition wall 8. This first chamber 221a is a gas outlet chamber through which gas G flows out. The left end opening of each of the hollow fiber membranes 31 (flow paths 32) of the hollow fiber membrane bundle 3A opens to and communicates with the first chamber 221a. Accordingly, the gas G flowing down inside each of the hollow fiber membranes 31 flows out to the first chamber 221a.

In addition, the gas outlet port 27 communicates with the first chamber 221a. An aspiration mechanism (not shown in the drawing) that aspirates the inside of the first chamber 221a is connected to this gas outlet port (connection port) 27. The aspiration mechanism is not particularly limited, and an example thereof includes wall aspiration. The wall aspiration is one of piping facilities of medical gas such as oxygen, therapeutic air, nitrogen, and aspiration, and it is possible to connect a connector of a piping for aspiration which is mounted on a wall or the like of an operating room to the gas outlet port 27. An aspiration force generated through an operation of this aspiration mechanism reduces the pressure in the first chamber 221a. Therefore, it is possible to reliably make the gas G flow down toward the first chamber 221a.

On the other hand, an annular rib 292 is also protrusively formed inside the second lid body 23A. A second chamber 231a is defined by the second lid body 23A, the rib 292, and the partition wall 9. This second chamber 231a is a gas inlet chamber through which gas G flows in. The right end opening of each of the hollow fiber membranes 31 of the hollow fiber membrane bundle 3A opens to and communicates with the second chamber 231a. Accordingly, it is possible to distribute the gas G from the second chamber 231a into each of the hollow fiber membranes 31.

In the artificial lung 10, a gas outlet portion is formed by the gas outlet port 27 and the first chamber 221a and is disposed on a left end side (the other end side) of the hollow fiber membrane bundle 3A. In addition, a gas inlet portion is formed by the gas inlet port 26 and the second chamber 231a and is disposed on a right end side (one end side) of the hollow fiber membrane bundle 3A. In this manner, in the artificial lung 10, the gas inlet portion and the gas outlet portion are respectively provided on an upstream side and a downstream side of the flow paths 32 while having a lumen of each of the hollow fiber membranes 31 as the flow path 32 (gas flow path). Accordingly, the flow of the gas G becomes linear, and thus, it is possible to make the gas promptly flow down.

As described above, all the hollow fiber membrane bundles 3A and 3B are constituted of a large number of hollow fiber membranes 31. The hollow fiber membrane bundle 3A and the hollow fiber membrane bundle 3B has the same hollow fiber membranes 31 even though the hollow fiber membrane bundle 3A is porous and the application of the hollow fiber membrane bundle 3A and the hollow fiber membrane bundle 3B are different from each other, and therefore, the outer hollow fiber membrane bundle 3A will be representatively described below.

The inner diameters φd1 of the hollow fiber membranes 31 are preferably 50 µm to 700 µm and more preferably 70 µm to 600 µm (refer to FIG. 6). The outer diameters φd2 of the hollow fiber membranes 31 are preferably 100 µm to 1000 µm and more preferably 120 µm to 800 µm (refer to FIG. 6). Furthermore, the ratio d1/d2 of the inner diameter φd1 to the outer diameter φd2 is preferably 0.5 to 0.9 and more preferably 0.6 to 0.8. In each of the hollow fiber membranes 31 having such conditions, it is possible to comparatively reduce the pressure loss when the gas G is made to flow in the flow paths 32 which are hollow portions of the hollow fiber membranes 31 while maintaining its strength, and such conditions also contribute to maintaining the winding state of the hollow fiber membranes 31. For example, when the inner diameter φd1 is larger than or equal to the upper limit value, the thickness of the hollow fiber membranes 31 becomes thin, and the strength of the hollow fiber membranes decreases in accordance with other conditions. In addition, when the inner diameter φd1 is smaller than the lower limit value, the pressure loss when the gas G is made to flow in the hollow fiber membranes 31 increases in accordance with other conditions.

In addition, the distance between adjacent hollow fiber membranes 31 is more preferably 1/10 to 1/1 of the φd2.

The method for manufacturing such hollow fiber membranes 31 is not particularly limited, but examples thereof include a method using extrusion molding, particularly a method using a stretching method or a solid-liquid phase separation method. It is possible to manufacture the hollow fiber membranes 31 having a predetermined inner diameter φd1 and a predetermined outer diameter φd2 through this method.

For example, as the constituent material of each of the hollow fiber membranes 31, hydrophobic polymer materials such as polypropylene, polyethylene, polysulfone, polyacrylonitrile, polytetrafluoroethylene, and polymethylpentene are used, a polyolefin resin is preferably used, and polypropylene is more preferably used. The selection of such resin materials contributes to maintaining the winding state of the hollow fiber membranes 31 and also to cost reduction during the manufacture of the hollow fiber membranes.

Here, the flow of the blood B in the artificial lung 10 of the present embodiment will be described. In this artificial lung 10, the blood B flowing in from the blood inlet port 201 flows into the heat exchange portion 10B after passing through the blood inflow side space 24A and the side holes 243 in order. In the heat exchange portion 10B, heat exchange (heating or cooling) is performed such that the blood B comes into contact with the surface of each of the hollow fiber membranes 31 of the heat exchange portion 10B while flowing through the blood flow paths 33 in a downstream direction. The blood B which has been subjected to heat exchange in this manner flows into the artificial lung portion 10A.

In the artificial lung portion 10A, the blood B flows through the blood flow paths 33 in a further downstream direction. On the other hand, gas (gas containing oxygen) supplied from the gas inlet port 26 is distributed from the second chamber 231a into the flow paths 32 of the hollow fiber membranes 31 of the artificial lung portion 10A, accumulated in the first chamber 221a after flowing through the flow path 32, and is discharged from the gas outlet port 27. The blood B flowing through the blood flow paths 33 comes into contact with the surface of each of the hollow fiber membranes 31 of the artificial lung portion 10A, and gas exchange, that is, addition of oxygen and decarbonation is performed between the blood and the gas G flowing through the flow paths 32.

In a case where air bubbles mixed with the blood B which has been subjected to gas exchange, these air bubbles are captured by the filter member 41A and are prevented from flowing out to the downstream side of the filter member 41A.

The blood B which has been subjected to the heat exchange and the gas exchange as described above in order and from which air bubbles are removed flow out using the blood outlet port 28.

Next, the method for manufacturing the artificial lung 10 will be described while referring to FIGS. 7 to 14. This preferred embodiment of the manufacturing method has a first forming step, a first mounting step, a second forming step, a second mounting step, a fixing step, and an assembling step.

A First Forming Step forms the hollow fiber membrane bundle 3B in an inner member 206 having the first cylindrical member 241 and the second cylindrical member 245. This step can be performed using a well-known winding device. Thus, it is possible to wind the hollow fiber membranes 31 around the irregular portion 244 of the first cylindrical member 241.

A First Mounting Step is a step of mounting the intermediate sheet member 11 on the hollow fiber membrane bundle 3B.

Figure 7:
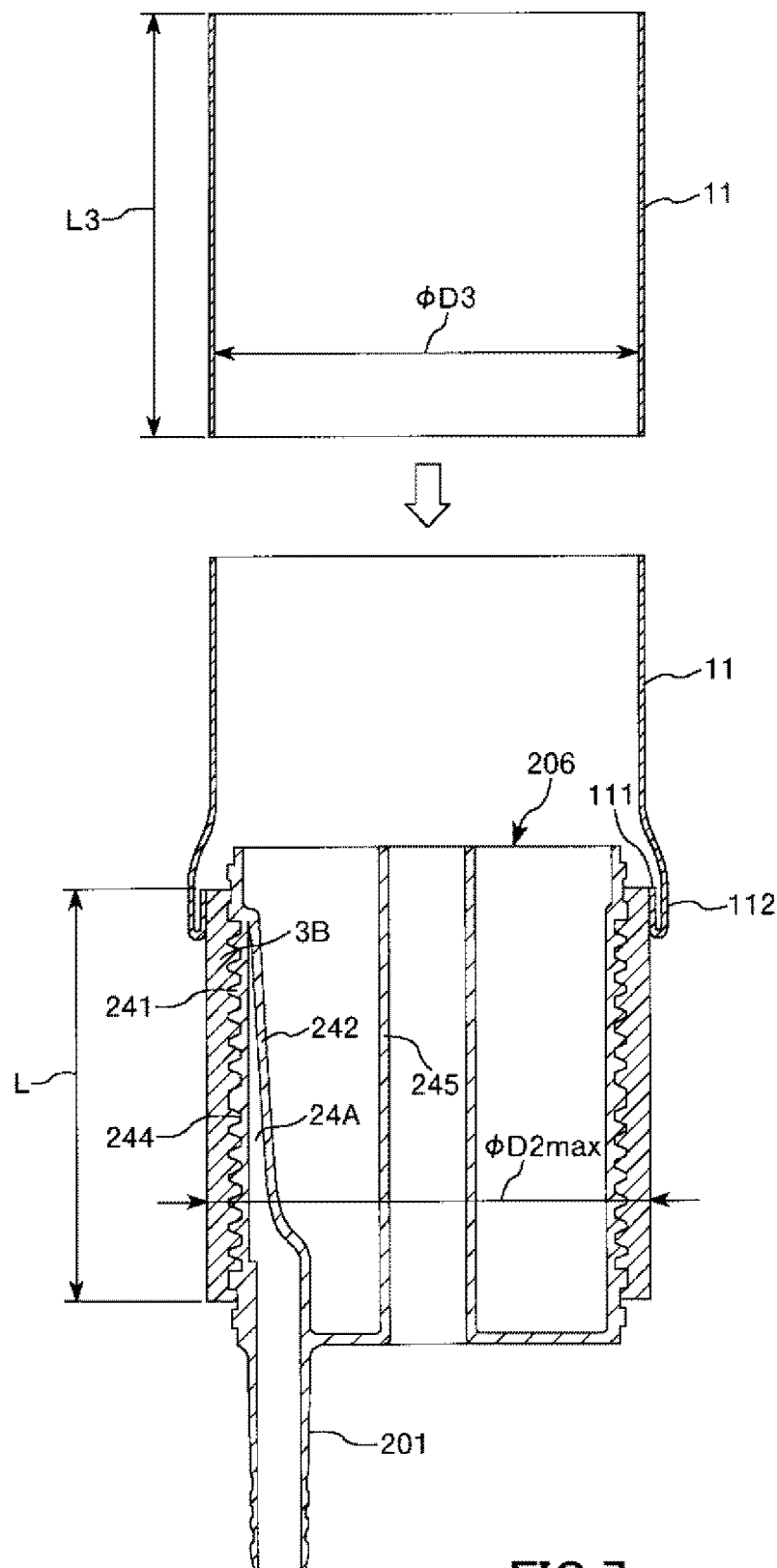
FIG. 7 is a longitudinal cross-sectional view showing a process of manufacturing the artificial lung shown in FIG. 1 in order.

As described above, the intermediate sheet member 11 forms a mesh shape. For this reason, the intermediate sheet member 11 is expandable. In addition, as shown in FIG. 7, the intermediate sheet member 11 is configured as a cylindrical member in advance (e.g., woven according to a cylindrical pattern). The inner diameter φD3 of the intermediate sheet member 11 in a case where the intermediate sheet member is in a cylindrical shape in a natural state where no external force is applied to the intermediate sheet member, that is, in a state before being mounted on the hollow fiber membrane bundle 3B is smaller than the maximum outer diameter φD2max of the hollow fiber membrane bundle 3B. As this φD3, for example, 91% to 99.9% of φD2max is preferable and 91% to 95% or 96% to 99% of φD2max is more preferable. In addition, the length L3 of the intermediate sheet member 11 along a central axis direction is preferably the same as or slightly smaller than the length L of the hollow fiber membrane bundle 3B.

First, the intermediate sheet member 11 is made to enter an inverted state (i.e., turned inside out) where the front and the back of the intermediate sheet member is inverted, prior to the mounting of the intermediate sheet member 11 on the hollow fiber membrane bundle 3B. A lower end portion of the intermediate sheet member 11 is folded back inward while maintaining this inverted state, and the folded-back portion 111 is fitted to (i.e., stretched over) the upper end portion of the hollow fiber membrane bundle 3B (refer to FIG. 7). The folded-back portion 111 is returned to an original state where the front and the back are not inverted.

Figure 8:
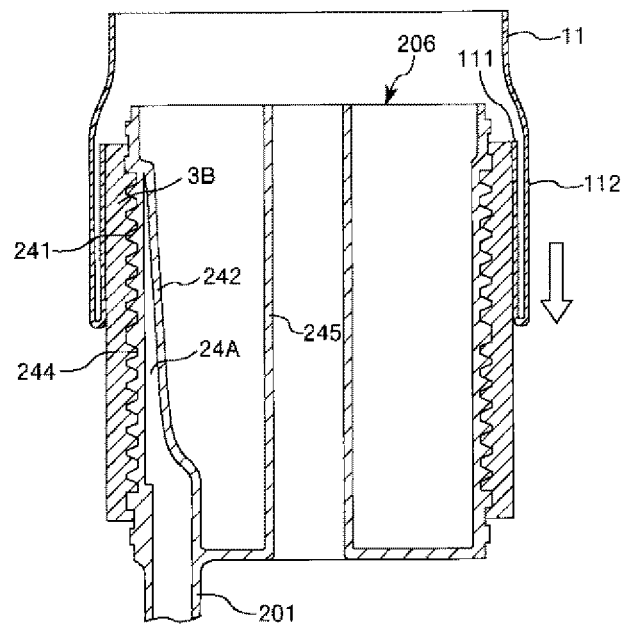
FIG. 8 is a longitudinal cross-sectional view showing the process of manufacturing the artificial lung shown in FIG. 1 in order.

Subsequently, as shown in FIG. 8, a portion (inverted portion 112) which is in the inverted state of the intermediate sheet member 11, that is, a portion on an outside of the folded-back portion 111 of the intermediate sheet member 11 is gradually slid downward so that the intermediate sheet member is returned to the original state where the front and the back are not inverted.

Figure 9:
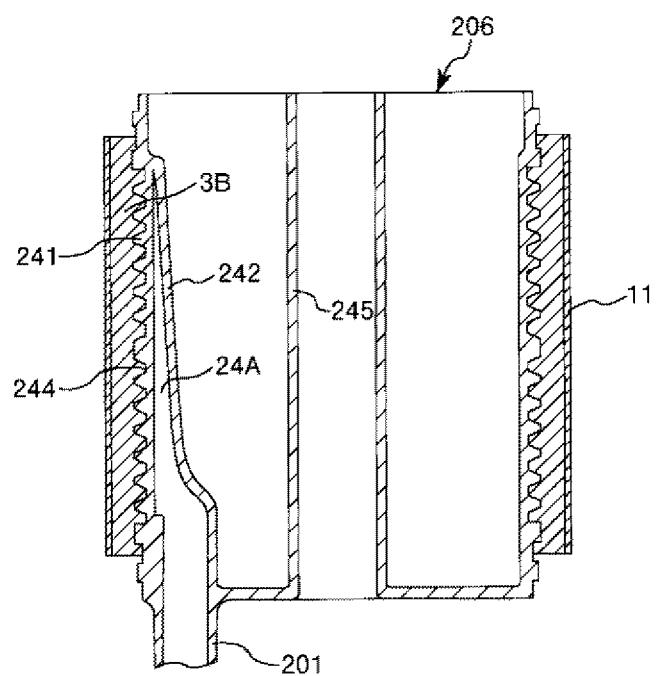
FIG. 9 is a longitudinal cross-sectional view showing the process of manufacturing the artificial lung shown in FIG. 1 in order.

When this work (operation) is continued, as shown in FIG. 9, the entirety of the intermediate sheet member 11 is returned to the state where the front and the back are not inverted, and the mounting of the intermediate sheet member on the hollow fiber membrane bundle 3B is completed.

In addition, as described above, the inner diameter φD3 of the intermediate sheet member 11 is smaller than the maximum outer diameter φD2max of the hollow fiber membrane bundle 3B. Accordingly, in the mounting process of the intermediate sheet member 11, the intermediate sheet member 11 can fasten the hollow fiber membrane bundle 3B in the direction from the outer peripheral portion side toward the central axis side, and this fastened state is maintained as it is even after the first mounting step (refer to arrow A11 in FIG. 5). Accordingly, it is possible to reliably bring the intermediate sheet member 11 into close contact with the hollow fiber membrane bundle 3B. Thus, it is possible to maintain the shape of the hollow fiber membrane bundle 3B and to easily perform the next step stably.

In addition, since the mounting of the intermediate sheet member 11 is performed while fastening the hollow fiber membrane bundle 3B using the intermediate sheet member 11, the mounting method performed so as to return the state where the front and the back are inverted to the original state contributes to facilitating the mounting work of the intermediate sheet member 11.

Figure 10:
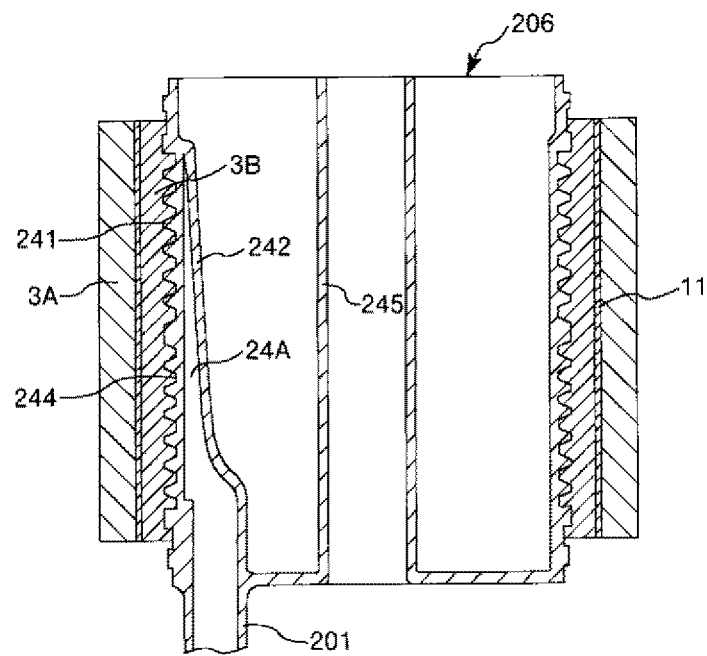
FIG. 10 is a longitudinal cross-sectional view showing the process of manufacturing the artificial lung shown in FIG. 1 in order.

A Second Forming Step is a step of forming the hollow fiber membrane bundle 3A on the intermediate sheet member 11. This step can be performed using a winding device similarly to the first forming step. Accordingly, it is possible to wind the hollow fiber membranes 31 on the intermediate sheet member 11, and thus, the hollow fiber membrane bundle 3A is formed as shown in FIG. 10.

In addition, the shape of the hollow fiber membrane bundle 3B is maintained by the intermediate sheet member 11, and therefore, it is possible to stably perform the winding of the hollow fiber membranes 31.

A Second Mounting Step is a step of mounting the filter member 41A on the hollow fiber membrane bundle 3A.

Figure 11:
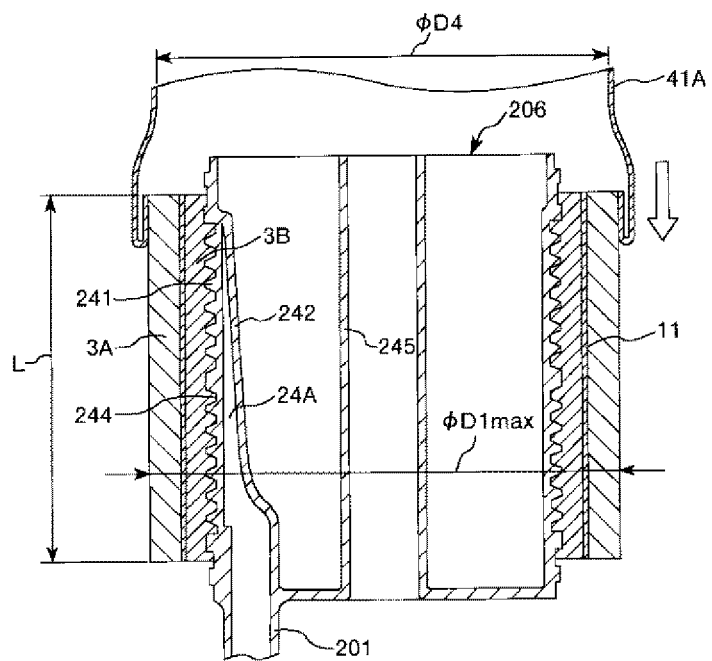
FIG. 11 is a longitudinal cross-sectional view showing the process of manufacturing the artificial lung shown in FIG. 1 in order.

As described above, the filter member 41A also forms a mesh shape. For this reason, the filter member 41A is expandable. In addition, as shown in FIG. 11, the filter member 41A is configured as a cylindrical member in advance (e.g., woven according to a cylindrical pattern). The inner diameter φD4 of the filter member 41A in a case where the filter member is in a cylindrical shape in a natural state where no external force is applied to the filter member is smaller than the maximum outer diameter φD1max of the hollow fiber membrane bundle 3A. As this φD4, for example, 90% to 96% of φD1max is preferable, 91% to 95% φD1max is more preferable, and or 92% to 95% of φD1max is still more preferable. In addition, the length of the filter member 41A along the central axis direction is preferably the same as or slightly smaller than the length L of the hollow fiber membrane bundle 3A.

Figure 12:
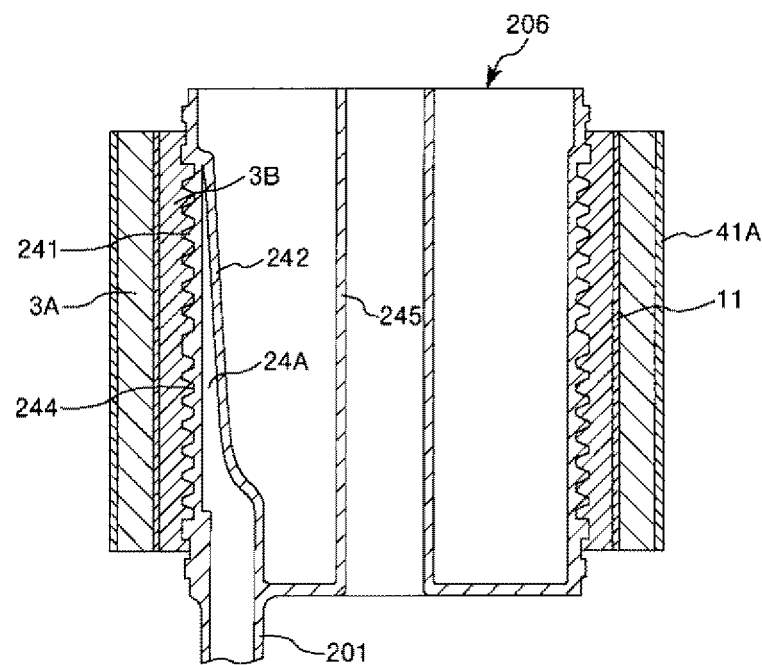
FIG. 12 is a longitudinal cross-sectional view showing the process of manufacturing the artificial lung shown in FIG. 1 in order.

The mounting of the filter member 41A on the hollow fiber membrane bundle 3A in this step is the same as that of the intermediate sheet member 11 on the hollow fiber membrane bundle 3A in the first mounting step. That is, the filter member 41A is made to enter an inverted state where the front and the back of the filter member is inverted, prior to the mounting of the filter member 41A on the hollow fiber membrane bundle 3A. The filter member 41A is mounted thereon such that this inverted state is returned to the original state where the front and the back are not inverted (refer to FIG. 11). Accordingly, as shown in FIG. 12, the entirety of the filter member 41A is returned to the state where the front and the back are not inverted, and the mounting of the filter member on the hollow fiber membrane bundle 3A is completed.

In addition, as described above, the inner diameter φD4 of the filter member 41A is smaller than the maximum outer diameter φD1max of the hollow fiber membrane bundle 3A. Accordingly, in the mounting process of the filter member 41A, the filter member 41A can fasten the hollow fiber membrane bundle 3A in the direction from the outer peripheral portion side toward the central axis side, and this fastened state is maintained as it is even after the second mounting step (refer to arrow A41A in FIG. 5). Accordingly, it is possible to reliably bring the filter member 41A into close contact with the hollow fiber membrane bundle 3A. Thus, it is possible to reliably exhibit an air bubble capturing function of the filter member 41A.

Note that a fastening degree (i.e., compression force) of the intermediate sheet member 11 with respect to the hollow fiber membrane bundle 3B is smaller than that of the filter member 41A with respect to the hollow fiber membrane bundle 3A. Accordingly, it is possible to prevent the hollow fiber membrane bundle 3B from being excessively fastened by the filter member 41A. Thus, it is possible to reliably prevent the hollow fiber membranes 31 or the blood flow paths 33 in the hollow fiber membrane bundle 3B from being blocked.

A Fixing Step is a step of collectively fixing the hollow fiber membrane bundle 3A, the hollow fiber membrane bundle 3B, the filter member 41A, and the intermediate sheet member 11 to the first cylindrical member 241.

Figure 13:
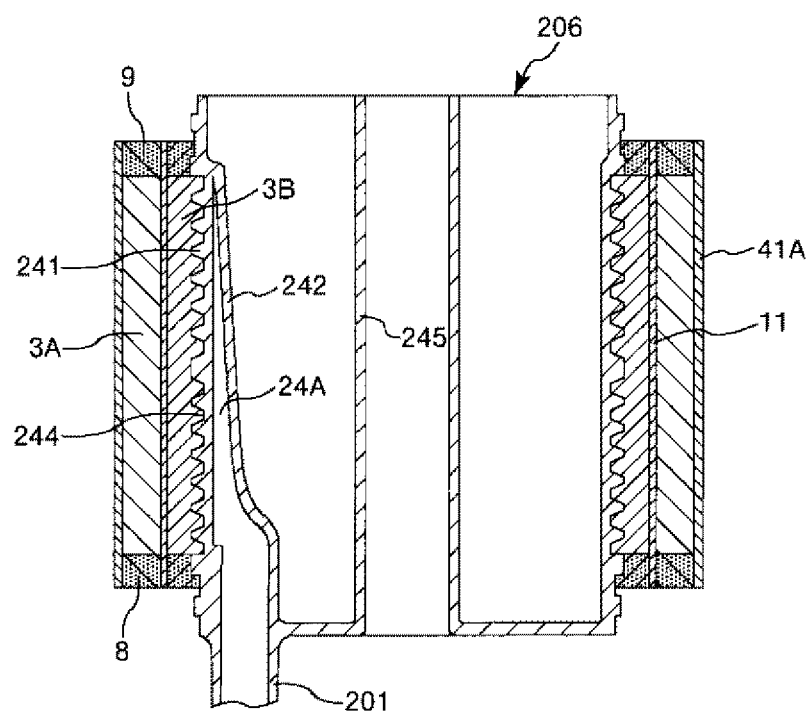
FIG. 13 is a longitudinal cross-sectional view showing the process of manufacturing the artificial lung shown in FIG. 1 in order.

First, the material constituting the partition wall 8 and the partition wall 9 is applied to a predetermined portion in a liquid state, and is then solidified. Accordingly, the hollow fiber membrane bundle 3A, the hollow fiber membrane bundle 3B, the filter member 41A, and the intermediate sheet member 11 are collectively fixed (e.g., potted) to the first cylindrical member through the partition wall 8 and the partition wall 9 as shown in FIG. 13.

An Assembling Step is a step of assembling the inner member 206, to which the hollow fiber membrane bundle 3A, the hollow fiber membrane bundle 3B, the filter member 41A, and the intermediate sheet member 11 are fixed, the cylindrical housing main body 21A, the first lid body 22A, and the second lid body 23A.

Figure 14:
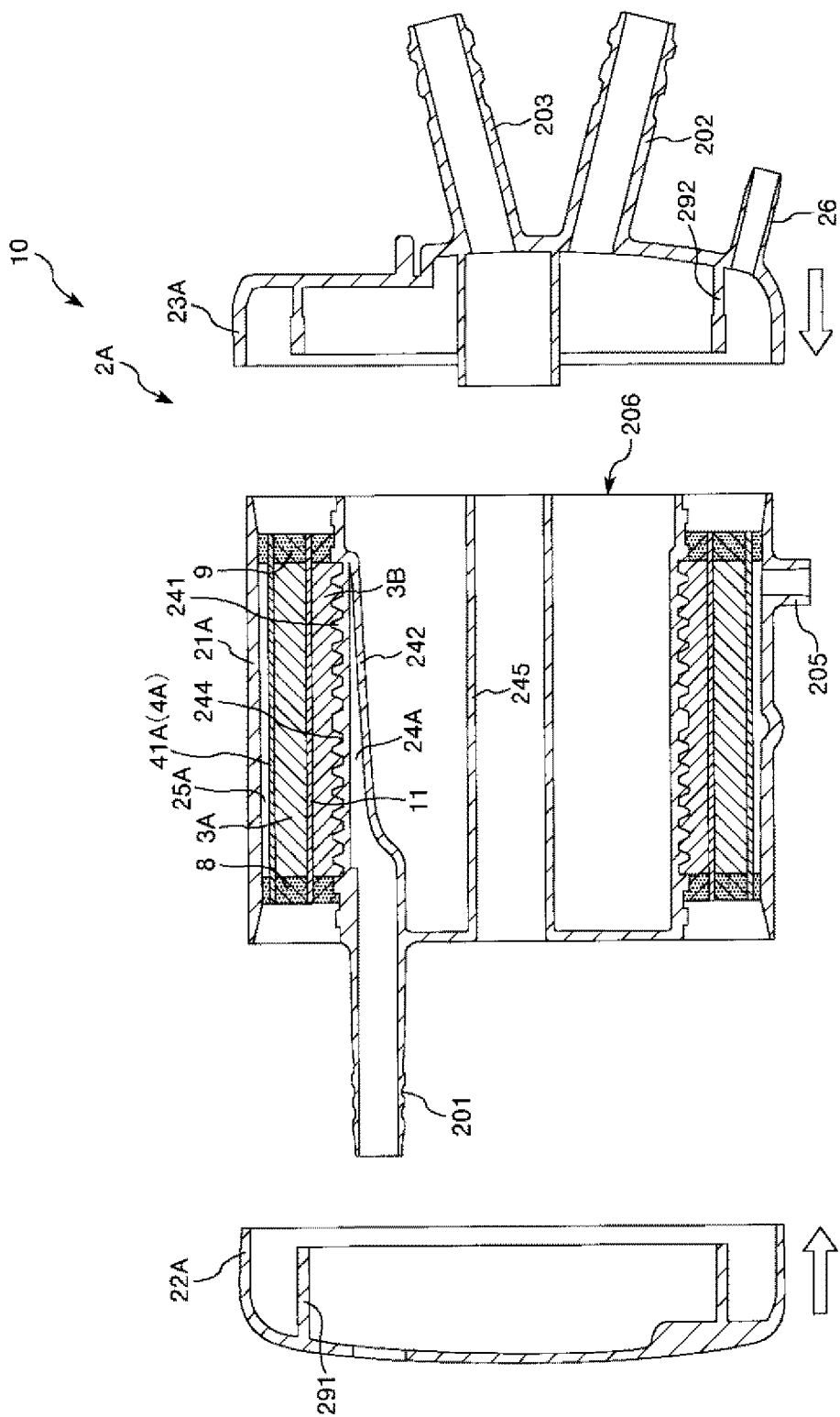
FIG. 14 is a longitudinal cross-sectional view showing the process of manufacturing the artificial lung shown in FIG. 1 in order.

First, the inner member 206 is housed in and fixed to the cylindrical housing main body 21A as shown in FIG. 14. Next, the first lid body 22A is mounted on and fixed to the inner member from the right side and the second lid body 23A is mounted on and fixed to the inner member from the left side. Accordingly, the artificial lung 10 is completed.

Note that the first mounting step and the second mounting step are preferably performed within an environment of generating positrons or positively charged ions. Accordingly, it is possible to prevent static electricity generated during mounting of the filter member 41A or the intermediate sheet member 11.

Second Embodiment

FIGS. 15 to 18 are longitudinal cross-sectional views showing the process (including the method for manufacturing a hollow-fiber-type blood processing device of the present invention) of manufacturing the artificial lung in order in a case where the hollow-fiber-type blood processing device of the present invention is applied to the artificial lung.

Hereinafter, a second embodiment of a method for manufacturing a hollow-fiber-type blood processing device of the present invention and the hollow-fiber-type blood processing device of the present invention will be described while referring to these drawings. However, the difference from the above-described embodiment will be mainly described and the description of the same matter will not be repeated.

The present embodiment is the same as the first embodiment except that the method for manufacturing an artificial lung is partially different from that in the first embodiment.

As shown in FIGS. 15 to 18, in the present embodiment, a release sheet 12 is used in a first mounting step. The release sheet 12 forms a band shape and the entire length thereof is sufficiently longer than the length of the entire circumference of the outer peripheral portion of the hollow fiber membrane bundle 3B. In addition, the length L4 of the release sheet 12 along the central axis direction of the hollow fiber membrane bundle 3B is also sufficiently longer than the length L of the hollow fiber membrane bundle 3B. In addition, the thickness of the release sheet 12 is preferably 0.05 to 0.2 mm and more preferably 0.1 to 0.13 mm.

Friction reduction processing for reducing friction is performed on both surfaces of this release sheet 12. Accordingly, it is possible to easily perform a releasing operation (removing operation) to be described below. The friction reduction processing is not particularly limited, and an example thereof includes a method for performing Teflon coating ("Teflon" is registered trademark). Accordingly, the releasing force during a releasing operation can be set to be, for example, less than 500 mN/100 cm.

Figure 15:
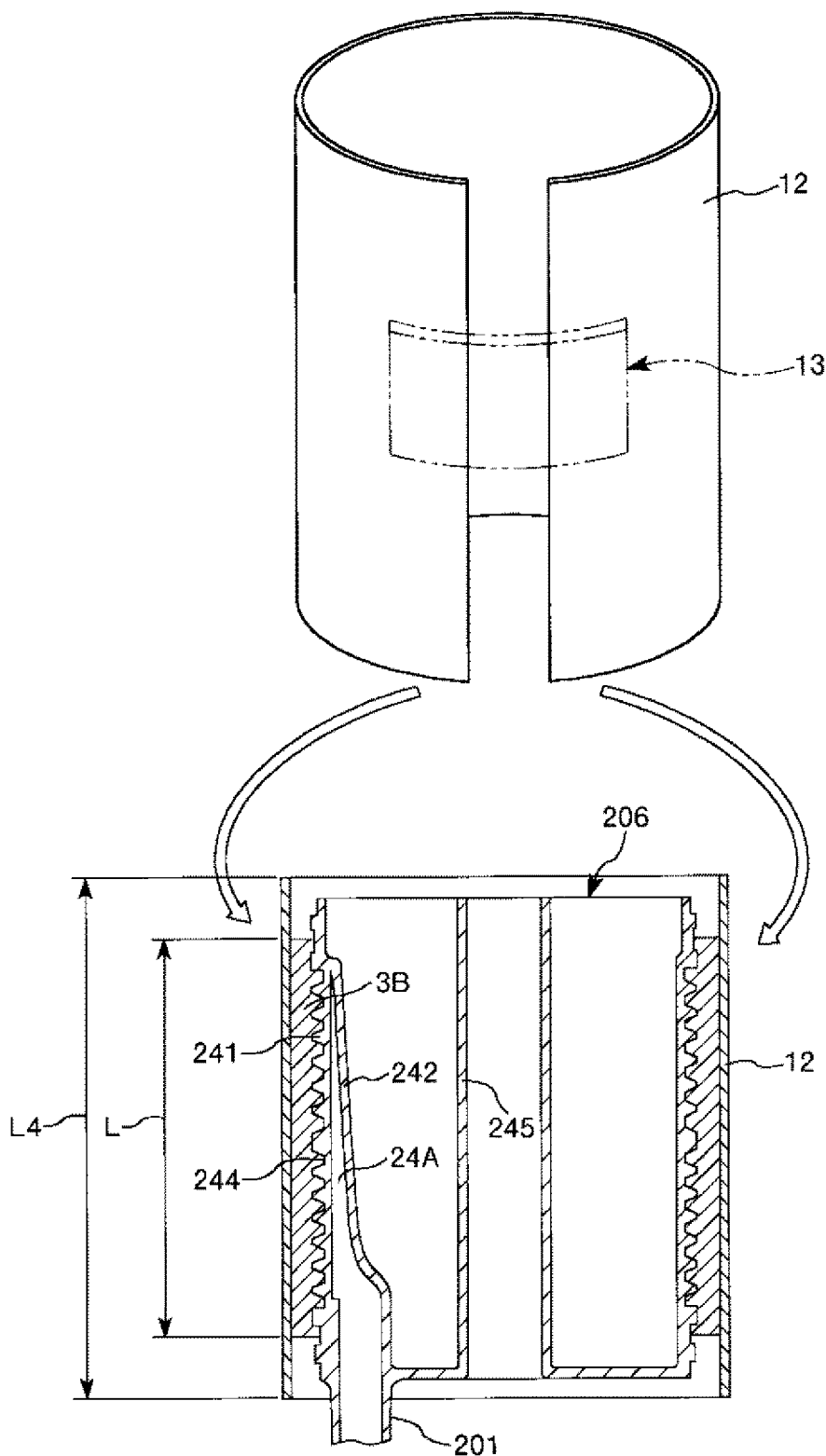
FIG. 15 is a longitudinal cross-sectional view showing the process of manufacturing the artificial lung in order in a case where the hollow-fiber-type blood processing device of the present invention is applied to the artificial lung.

First, as shown in FIG. 15, the release sheet 12 is wound around the entire circumference of the outer peripheral portion of the hollow fiber membrane bundle 3B prior to the mounting of the intermediate sheet member 11. In addition, a support member 13 constituted of a curved plate member is placed on a joint of both end portions of the release sheet 12. Accordingly, it is possible to prevent the release sheet 12 from spreading and falling off from the hollow fiber membrane bundle 3B.

Figure 16:
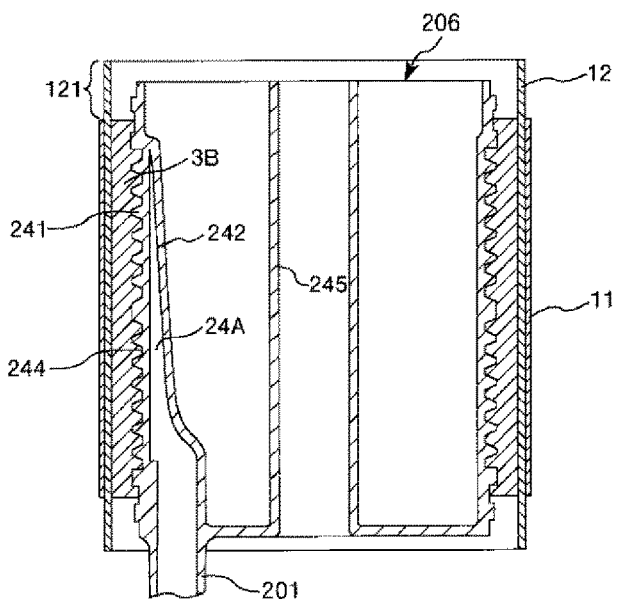
FIG. 16 is a longitudinal cross-sectional view showing the process of manufacturing the artificial lung in order in a case where the hollow-fiber-type blood processing device of the present invention is applied to the artificial lung.

Next, the intermediate sheet member 11 is mounted on the release sheet 12 once in an overlapping manner as shown in FIG. 16. The mounting at this time may be performed in a state where the front and the back are inverted as in first embodiment or may be performed in a state where the front and the back are kept intact without being inverted.

Figure 17:
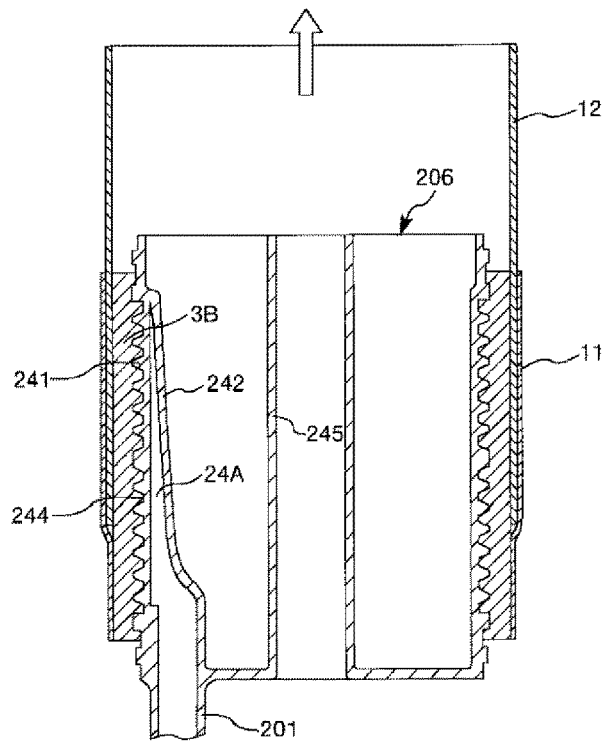
FIG. 17 is a longitudinal cross-sectional view showing the process of manufacturing the artificial lung in order in a case where the hollow-fiber-type blood processing device of the present invention is applied to the artificial lung.

Next, the release sheet 12 is pulled upward while living the intermediate sheet member 11 at its position as shown in FIG. 17. Note that the release sheet 12 has a portion 121 protruding upward from the intermediate sheet member 11 (refer to FIG. 16). Accordingly, it is possible to easily perform the pulling operation reliably while pinching the portion 121 with fingertips.

Figure 18:
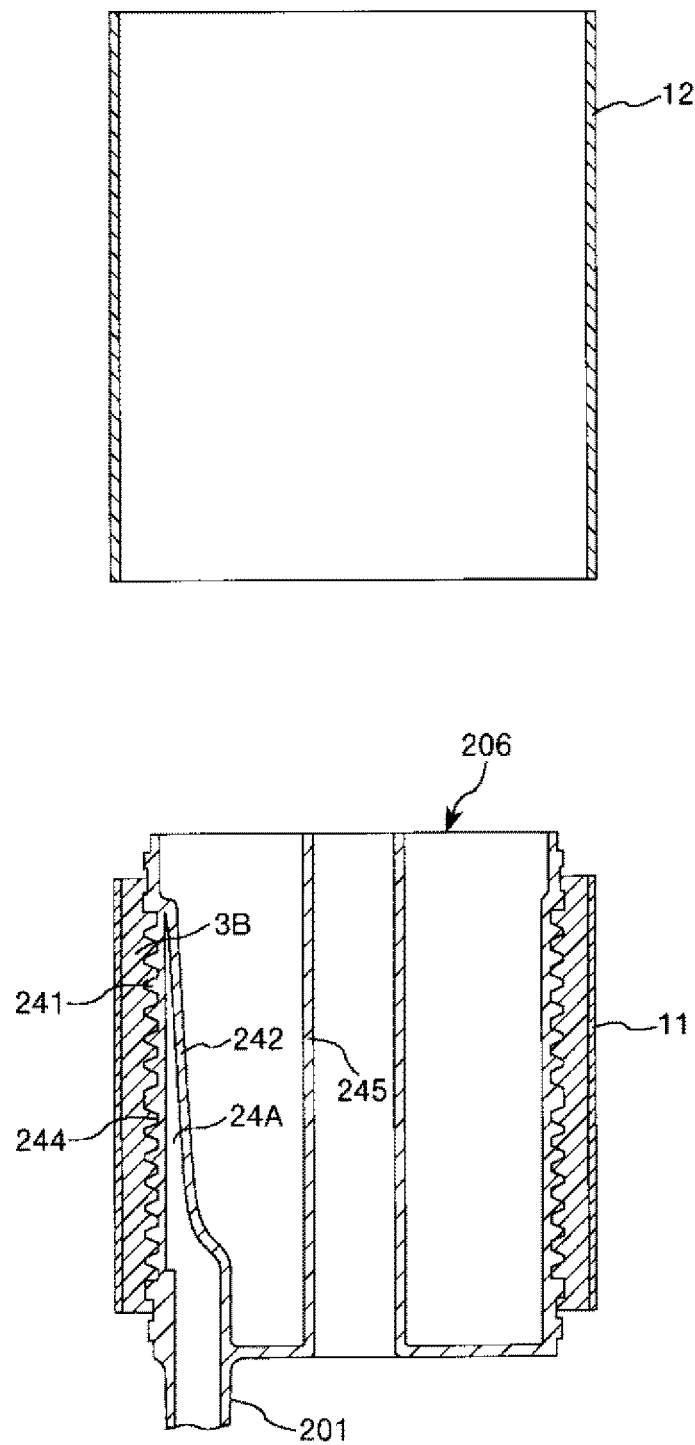
FIG. 18 is a longitudinal cross-sectional view showing the process of manufacturing the artificial lung in order in a case where the hollow-fiber-type blood processing device of the present invention is applied to the artificial lung.

By continuing this pulling operation, it is possible to release, that is, remove the release sheet 12 as shown in FIG. 18, and therefore, the intermediate sheet member 11 is mounted on the hollow fiber membrane bundle 3B.

Note that it is possible to mount the filter member 41A on the hollow fiber membrane bundle 3A similarly in the second mounting step using the release sheet 12.

The embodiments in which the method for manufacturing a hollow-fiber-type blood processing device of the present invention and the hollow-fiber-type blood processing device of the present invention are shown in the drawings have been described. However, the present invention is not limited thereto and each portion constituting the hollow-fiber-type blood processing device can be replaced with an arbitrary configuration that can exhibit the same function. In addition, an arbitrary structure may be added thereto.

In addition, the method for manufacturing a hollow-fiber-type blood processing device of the present invention and the hollow-fiber-type blood processing device of the present invention may be obtained by combining two or more arbitrary configurations (characteristics) of each of the embodiments.

In addition, each of the hollow fiber membranes constituting the hollow fiber membrane bundle of the artificial lung portion and each of the hollow fiber membranes constituting the hollow fiber membrane bundle of the heat exchange portion were the same as each other in the embodiments, but the present invention is not limited thereto. For example, one (former) hollow fiber membrane side (inner or outer bundle) may be thinner than the other (latter) hollow fiber membrane side (outer or inner bundle), or both hollow fiber membrane bundles may be formed of materials different from each other.

In addition, in the artificial lung portion and the heat exchange portion, the heat exchange portion is disposed inside and the artificial lung portion is disposed outside in the embodiments. However, the present invention is not limited thereto, and the artificial lung portion may be disposed inside and the heat exchange portion may be disposed outside. In this case, blood flows down from the outside to the inside.

In addition, the artificial lung portion and the heat exchange portion are formed of the hollow fiber membrane bundle, that is, a resin material in the embodiments. However, the present invention is not limited thereto, and a part or all of the heat exchange portion may be formed of a metal material.

The outer shape of each of the hollow fiber membrane bundle of the artificial lung portion and the hollow fiber membrane bundle of the heat exchange portion in the embodiments is formed in a cylindrical shape, but the present invention is not limited thereto. For example, the outer shape of the hollow fiber membrane bundle of the artificial lung portion may be formed in a cylindrical shape and the outer shape of the hollow fiber membrane bundle of the heat exchange portion may be formed in a columnar shape.

In addition, the method for manufacturing a hollow-fiber-type blood processing device of the present invention and the hollow-fiber-type blood processing device of the present invention can also be applied to, for example, a dialyzer for dialysis in addition to the artificial lung.

INDUSTRIAL APPLICABILITY

The method for manufacturing a hollow-fiber-type blood processing device of the present invention is a method for manufacturing a hollow-fiber-type blood processing device including a hollow fiber membrane bundle, which is obtained by bundling a large number of hollow fiber membranes to have an outer shape formed in a cylindrical shape or a columnar shape, and a sheet body mounted on the outer peripheral portion of the hollow fiber membrane bundle, the method includes: a mounting step of mounting the sheet body on the outer peripheral portion of the hollow fiber membrane bundle, in which when performing the mounting step, the sheet material is mounted in a state where the sheet material is previously formed as a cylindrical member. For this reason, the hollow fiber membrane bundle can be reliably brought into close contact with the sheet body. Accordingly, the method for manufacturing a hollow-fiber-type blood processing device of the present invention has industrial applicability.

What is claimed is:

1. A method for manufacturing a hollow-fiber-type blood processing device, comprising the steps of:
    forming a plurality of hollow fiber membranes into a bundle having an outer columnar shape;
    mounting a release sheet on an outer peripheral portion of the hollow fiber membrane bundle over its whole circumference;
    forming a sheet material into a cylindrical sheet body adapted to capture air bubbles to prevent the air bubbles from passing through the cylindrical sheet body when processing the blood, wherein the sheet material is expandable, and wherein an inner diameter of the cylindrical sheet body in its natural state where no external force is being applied is less than an outer diameter of the peripheral portion of the hollow fiber membrane bundle;
    mounting the sheet body onto a peripheral portion of the bundle, wherein the sheet body is mounted on the release sheet in an overlapping manner; and
    removing the release sheet while leaving the sheet body.

2. The method for manufacturing a hollow-fiber-type blood processing device according to claim 1,
    wherein the mounting of the sheet body holds the hollow fiber membrane bundle radially inwardly.

3. The method for manufacturing a hollow-fiber-type blood processing device according to claim 1,
    wherein the mounting step is comprised of a) configuring the sheet body into an inverted state where inner and outer surfaces of the sheet body are inverted, b) folding an edge of the sheet body over upon itself into an interior of the sheet body, c) stretching the folded edge and placing the folded edge onto the outer peripheral portion of the bundle, and d) sliding the sheet body over the folded edge and along the outer peripheral portion of the bundle to return the inverted state to an original state where the inner and outer surfaces of the sheet body are not inverted.

4. The method for manufacturing a hollow-fiber-type blood processing device according to claim 1,
    wherein friction reduction processing for reducing friction is performed on both surfaces of the release sheet.

5. The method for manufacturing a hollow-fiber-type blood processing device according to claim 1,
    wherein the sheet material is comprised of a fabric woven to an expandable mesh shape.

6. A hollow-fiber-type blood processing device comprising:
    a hollow fiber membrane bundle comprised of a plurality of hollow fiber membranes bundled into a columnar shape, wherein the hollow fiber membrane bundle includes an inner hollow fiber membrane bundle and an outer hollow fiber membrane bundle which are concentrically disposed with each other; and
    a sheet body mounted on an outer peripheral portion of the hollow fiber membrane bundle, wherein the sheet body is adapted to capture air bubbles to prevent the air bubbles from passing through the cylindrical sheet body when processing the blood, wherein the sheet body is comprised of a woven sheet material forming an expandable mesh, wherein the sheet body includes an inner sheet body mounted on the outer peripheral portion of the inner hollow fiber membrane bundle and an outer sheet body mounted on the outer peripheral portion of the outer hollow fiber membrane bundle;
    wherein the mounting of the sheet body is performed in a state where the hollow fiber membrane bundle is compressed by the sheet body in a direction from the outer peripheral portion side of the hollow fiber membrane bundle toward a central axis, and wherein a compression force of the inner sheet body with respect to the inner hollow fiber membrane bundle is smaller than that of the outer sheet body with respect to the outer hollow fiber membrane bundle.

7. The hollow-fiber-type blood processing device according to claim 6,
    wherein each of the inner sheet body and the outer sheet body forms a mesh shape, and
    wherein mesh openings of the inner sheet body are larger than mesh openings of the outer sheet body.

8. The hollow-fiber-type blood processing device according to claim 6,
    wherein the hollow fiber membrane bundle is configured to allow blood to pass between the hollow fiber membranes and has a heat exchange function of exchanging heat with blood passing through the device.

9. The hollow-fiber-type blood processing device according to claim 8 which comprises an artificial lung.

10. A method of manufacturing a blood processing device, comprising the steps of:
    winding a plurality of hollow fiber membranes onto a cylindrical support member to form a membrane bundle having a generally cylindrical shape;
    mounting a release sheet on the outer peripheral portion of the hollow fiber membrane bundle;
    forming a woven sheet material into an expandable cylindrical sheet body, wherein the sheet body has an unexpanded cylindrical diameter smaller than an outer diameter of the membrane bundle;
    stretching the sheet body over a peripheral portion of the bundle and onto the release sheet in an overlapping manner so that the sheet body compresses the membrane bundle; and
    removing the release sheet while leaving the sheet body in place by sliding out the release sheet.

11. The method of claim 10 wherein the stretching step is comprised of:
    folding an edge of the sheet body into an interior of the sheet body;
    stretching the folded edge onto the peripheral portion of the bundle; and
    sliding a remaining portion of the sheet body over the folded edge so that the sheet body is unfolded over the membrane bundle.

* * * * *